United States Patent [19]

Slaker

[11] 3,980,891

[45] Sept. 14, 1976

[54] METHOD AND APPARATUS FOR A ROTARY SCANNER FLAW DETECTION SYSTEM

[75] Inventor: Frank A. Slaker, Norwalk, Conn.

[73] Assignee: Intec Corporation, Norwalk, Conn.

[22] Filed: May 16, 1975

[21] Appl. No.: 578,276

[52] U.S. Cl. .............................. 250/563; 356/200
[51] Int. Cl.² ......................................... G01N 21/32
[58] Field of Search ........... 250/560, 561, 562, 563, 250/571, 572; 178/DIG. 3; 356/199, 200, 237, 239; 235/92 V

[56] References Cited
UNITED STATES PATENTS

| | | | |
|---|---|---|---|
| 3,060,319 | 10/1962 | Greunke | 250/571 |
| 3,222,979 | 12/1965 | Webster | 250/560 |
| 3,410,643 | 11/1968 | Jorgensen | 250/563 |
| 3,849,661 | 11/1974 | Beiter | 235/92 V |
| 3,898,469 | 8/1975 | Nichols et al. | 235/92 V |
| 3,900,265 | 8/1975 | Merlen et al. | 356/200 |

*Primary Examiner*—David C. Nelms
*Attorney, Agent, or Firm*—Joseph Levinson

[57] ABSTRACT

A rotary scan flaw detection system is provided in which a record medium is driven synchronously with the scanning of a source of radiation across the surface of material being examined for flaws. A method and apparatus are provided for dividing the material into discrete segments or strips so that flaw information obtained from scanning the material may be sorted and routed pursuant to a predetermined plan. A grating is scanned having predetermined marks thereon which are recorded on the record medium. The material is then scanned, the marks played back, and fed to a data routing logic circuitry along with the flaw information derived from the surface of the material being examined, so that the flaw information is automatically routed in accordance with the occurrence of flaws on discrete segments of the material.

8 Claims, 4 Drawing Figures

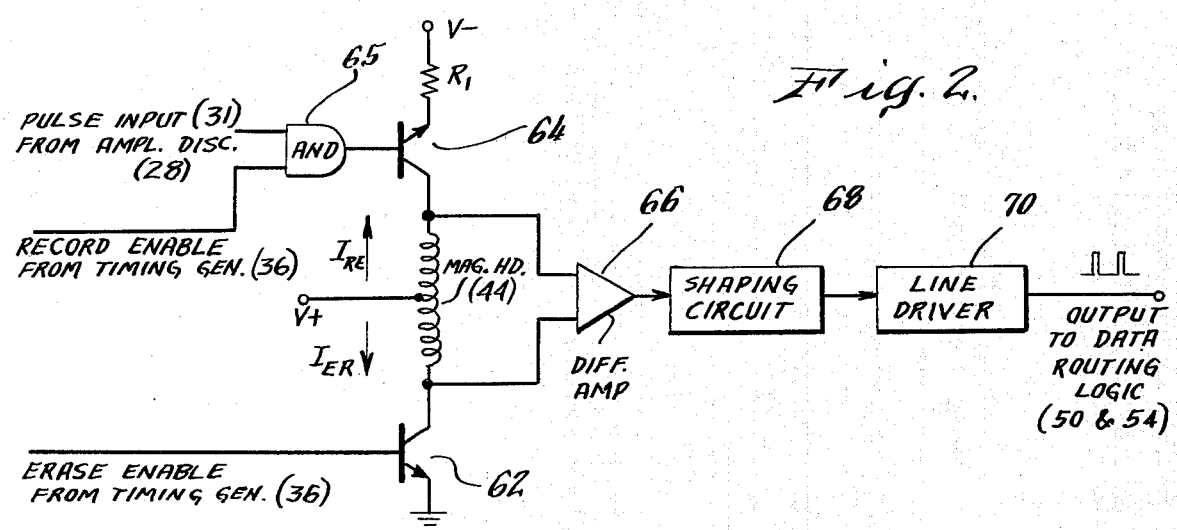
Fig. 2.
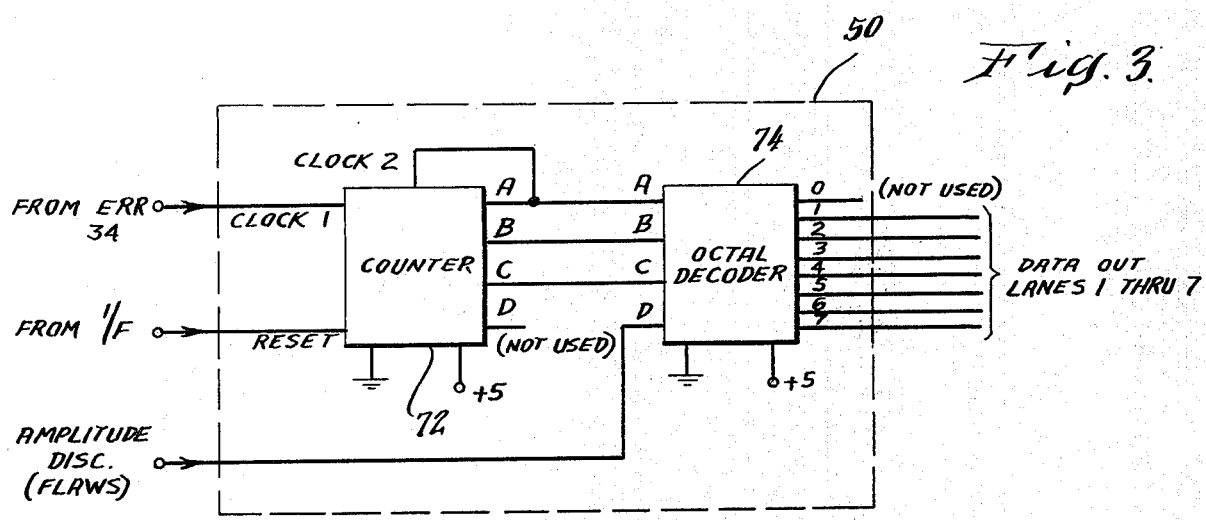
Fig. 3.
Fig. 4.

METHOD AND APPARATUS FOR A ROTARY SCANNER FLAW DETECTION SYSTEM

BACKGROUND OF THE INVENTION

This invention relates to a rotary scanner flaw detection system for the detection of flaws on a moving sheet or web of material, and more particularly to such a system having a record medium memory means driven in synchronism with the scanner which is utilized for dividing the material electrically into discrete segments or strips for providing a means of sorting or routing flaw information from the material in order to determine readily where the flaws occur on the material being examined.

The present invention has application to the type of flaw detection system shown and described in U.S. Pat. No. 3,781,531 issued Dec. 25, 1973, and patent application Ser. No. 449,247, filed Mar. 8, 1974, now U.S. Pat. No. 3,900,265, and patent application Ser. No. 465,510 filed Apr. 30, 1974, now U.S. Pat. No. 3,920,970, all of which are assigned to the assignee of the present invention. In the aforesaid systems, flaws are detected on the surface of the material being examined by repetitively scanning a suitable source of radiation, such as a laser beam, across the surface of the material. The laser light is reflected, transmitted, or scattered from the material, depending on the characteristics of the material, which light is picked up by a receiver having a suitable detector such as a photomultiplier tube. At any instant of time during the scan, the photomultiplier output varies with the reflectivity, transmissivity, or scattering properties of the spot on the material upon which the laser beam is impinging, and deviations from normal variation provide a means for indicating the material flaws. For many applications it is desirable to readily determine on what portion of the sheet of material or web the flaws occur, the number of flaws occurring on a specific portion of the web, the repetition rate, etc. For example, the web of material may be plastic, paper, magnetic tape, etc., which is manufactured in a wider web than will ultimately be used, but is so manufactured for uniformity's sake and the savings in manufacturing cost in not having to make a plurality of webs in narrower widths. If flaw information is readily available which is related to the strips into which the web will be divided, then only the faulty strips or portions of the web need be discarded, thereby saving the areas of material which are unflawed. Furthermore, in the manufacturing process, if a flaw continues to exist along a certain strip or segment, it may be desirable to examine the manufacturing process pertaining to the area where the flaw continues to occur, to locate the portion of the manufacturing process which is faulty and producing flaws on the material.

One solution to the problem is to provide a multiplicity of systems which only scan predetermined portions of the web of moving material. This approach would be extremely expensive in the duplication of equipment as well as being unwieldy and difficult to implement, particularly if the web is to be divided into a large number of segments.

A more practical solution to the problem is disclosed in an application Ser. No. 475,189, filed May 31, 1974, entitled "Data Router for a Flaw Detection System," now U.S. Pat. No. 3,898,469, which is assigned to the assignee of the present invention. The laser scan inspection system of the aforesaid application segregates the extracted data in accordance with the section of the web in which a flaw occurs by the use of a digital selection system utilizing thumb-wheel switches. The thumb-wheel switches are utilized to establish markers or positions which identify the sections, strips, or lanes of the web on which flaw information is to be extracted. Since the scanning of a flat surface is not linear even when using a rotary scanner, the thumb-wheel switches are set utilizing some form of grating or marking which may be made directly on the material being examined, or on a separate material where the markers show up as signals on the detector output. The data routing system of the aforesaid application may be quite acceptable for the case where the web is to be divided into a relatively few strips or sections. A practical limit, however, exists, for example from one to approximately eight lanes, due to the amount of space required for the switches and their associated circuitry. Beyond this point a profusion of switches and components, along with the potential for error, makes this approach less practical. Since the primary function of the selector thumb-wheel switches is that of a mechanical memory, any other form of non-volatile, synchronized, and spatially correlated memory would represent a dramatic improvement in reducing the complexity of the equipment utilizing and providing a data-routing function.

OBJECTS AND SUMMARY OF THE INVENTION

Accordingly, it is an object of this invention to provide a new and improved method and apparatus for providing a data routing function for a flaw detection system.

A further object of this invention is to provide a new and improved rotary scanner flaw detection system providing a data routing function which is simple to operate, greatly expands the data routing capabilities of the system, and greatly simplifies the technique of data routing.

Still another object of this invention is to provide a new and improved data routing system for a rotary scan inspection system which provides a simple method for changing the data routing function in accordance with the different widths of material being inspected, or with the desires of the operator.

In carrying out this invention in one illustrative embodiment thereof, a record medium is provided which is driven synchronously with the scanning of a source across the surface of material being examined for flaws. A suitable grating is prepared having marks thereon in predetermined position which are capable of being detected and passed by the flaw detection system. The grating is scanned, and the marks are detected in accordance with their predetermined position on the grating which corresponds to a predetermined position on the material being examined. The marks are synchronously recorded on the record medium and then played back in synchronism with the scanning of the surface of the material being examined for flaws. The detected flaws and marks are fed to data routing logic circuitry so that the flaw information is automatically routed and sorted in accordance with the occurrence of the flaws on discrete strips or lanes of the material.

BRIEF DESCRIPTION OF THE DRAWINGS

FIG. 2 shows one form of erase/record/replay circuitry which may be utilized in the flaw detection system of FIG. 1.

FIG. 3 illustrates the form of data routing logic circuitry which may be used in the flaw detection system of FIG. 1.

FIG. 4 illustrates a series of timing signals useful in explaining the operation of FIG. 3.

FIG. 5 shows an alternative embodiment of a magnetic encoder which may be utilized in the system shown in FIG. 1.

DESCRIPTION OF THE PREFERRED EMBODIMENTS

Figure 1:
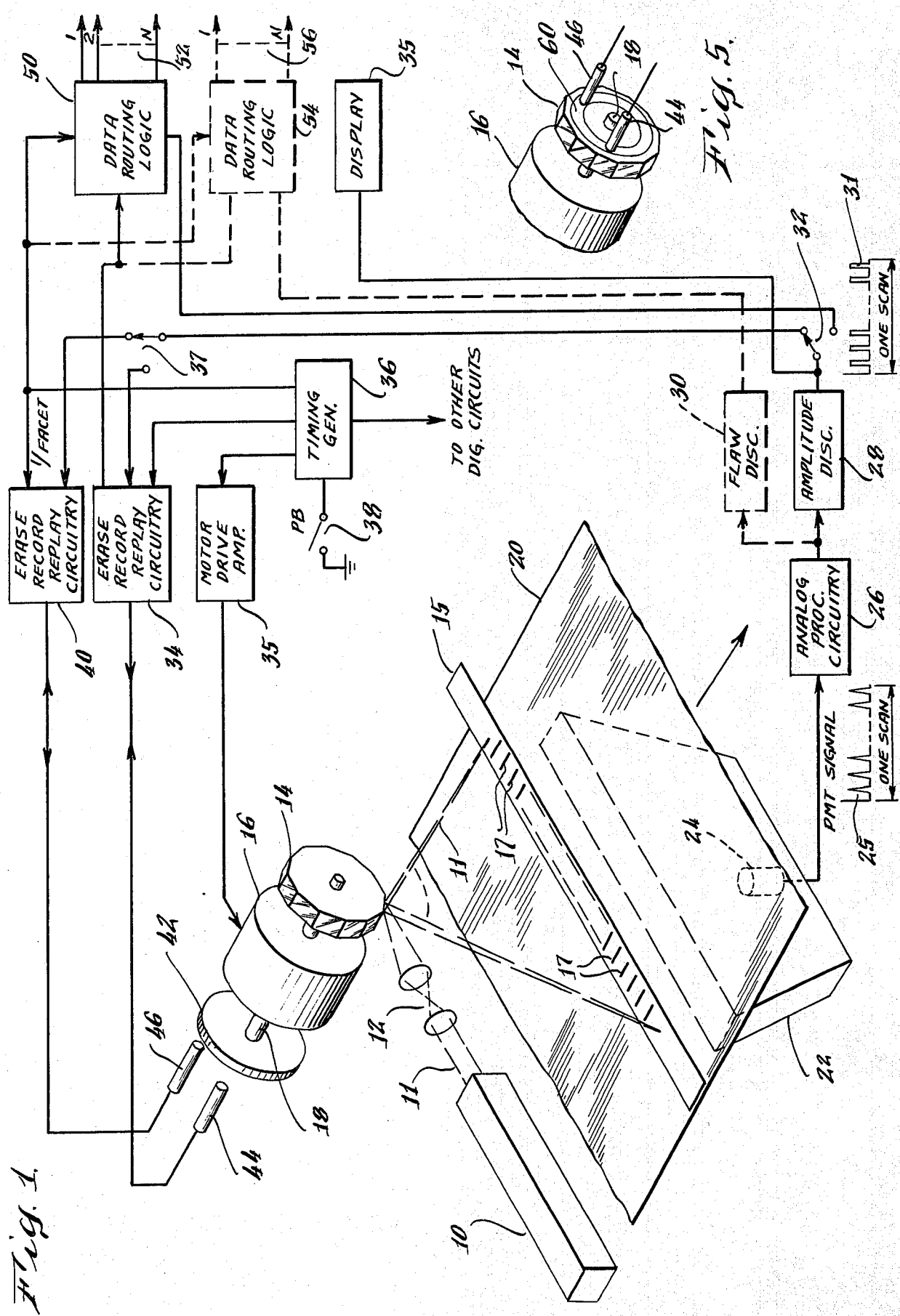
FIG. 1 is a diagrammatic representation of the rotary scan flaw detection system embodied in this invention, with the circuitry incorporated therein represented in block form.

Referring now to FIG. 1, a suitable source of radiation, for example a light beam 11 generated by a laser 10, is applied by a suitable spot-forming optics 12 to a scanner 14. The scanner 14 is a conventional multi-facet mirrored surface polygon which is driven by a motor 16 via a motor shaft 18. The rotary scanner 14 performs the function of successively scanning the laser beam 11 across a web or sheet of material 20 which is continuously moving in the direction shown by the arrow on the drawing. The rotary scanner 14 causes the beam 11 to scan across the surface of the material 20 and scanning in the orthogonal direction to create a raster is accomplished automatically by the movement of the web of material 20. Light transmitted through the material 20 is applied to a receiver 22 having a suitable detector 24 therein, such as a photomultiplier tube, which detects the light applied thereto. At any instant of time during the scan, the detector 24 provides an output which is proportional to the transmission of the spot on the material 20 on which the laser beam 11 is impinging. Flaws occurring on the surface of the material 20 being examined change the output of the detector 24 due to the transmissive properties of the material being examined, providing a means for indicating flaws on the surface of the material 20. Although different types of receivers may be utilized, one form which is suitable for the present application is shown and described in application Ser. No. 449,247 referred to above. Although a transmission type system is illustrated for purposes of disclosure, a reflective type system where the output of the detector 24 is proportional to the reflectivity of the spot on which the laser beam is impinging is also applicable to the present invention. Whether a transmissive or reflective mode is utilized will depend on the application and the type of material being examined.

A grating 15 having a series of marks 17 is shown on the drawing positioned above the receiver 22. The grating 15 whose function will be described hereinafter may in its simplest form consist of marks 17 placed directly on the surface of material 20, or may be in the form of a separate grating or template 15 which is positioned over the receiver with the marks 17 arranged in predetermined fashion to represent demarcation lines in the data router processing of the actual web being inspected. For the transmission mode illustrated, other than the simple grating already described, a black plastic strip may be utilized which has a multiplicity of clear slits which are positioned in accordance with the desired data routing function. When operating in the reflective mode, other than the simplest grating comprising marks on a white paper or on the surface of the material 20, reflective marks could be utilized.

Signals such as those indicated by reference numeral 25 in the drawing, which actually depict the detection of the marks 17, are applied from the detector 24 to analog processing circuitry 26 which amplifies and otherwise processes the signals for application to an amplitude discriminator 28. The analog processing circuitry 26 may include circuitry such as that shown in application Ser. No. 465,510 referred to above. The amplitude discriminator 28 passes only those signals which exceed a predetermined amplitude, which outputs are then considered flaw signals which are desired to be displayed on a suitable display 35, such as on an oscilloscope, and otherwise further processed, counted, or stored. Signals 31, which represent the marks 17, characterize the output from the amplitude discriminator 28. The amplitude discriminator 28 is coupled to the display 35 which provides a visual presentation of the flaws as they occur during the scan, and the signals are also applied via a switch 32 to data routing logic 50 for further processing. A plurality of other flaw discriminators may be provided, one being indicated in dotted lines as flaw discriminator 30, which may be designed to pass flaws having different characteristics, for example, different polarities, widths, lengths, etc.

The description up to this point is considered conventional. What will now be described is the synchronized magnetic memory which provides a means for recording the marks to delineate predetermined portions of the material 20 being examined, so that a suitable data routing method and system may be provided by playing back the marks as the material is being examined, and utilizing the playback to control the data routing function.

The memory consists of a suitable recording medium, such as a magnetic disk 42 mounted on and driven by the motor shaft 18. Since the rotary scanner 14 and the magnetic disk 42 are both driven by the motor 16 through a common shaft 18, the disk 42 is driven synchronously with the rotating scanner 14. The magnetic disk 42 has a pair of magnetic heads 44 and 46 coupled to either the disk face or periphery so as to form two magnetic read/record tracks. Magnetic heads 44 and 46 are in turn connected to erase/record/replay circuts (ERR) 34 and 40, respectively. A timing generator 36 provides a signal which is coupled to a motor drive amplifier 35 for driving the motor 16. Timing generator 36 is also coupled to the ERR circuitry 34 and 40 for controlling the timing and operation thereof. The ERR circuitry 34 and 40 are coupled to a data routing logic circuit 50 which also has coupled thereto the output from the flaw discriminator 28. The data routing logic 50 has a plurality of outputs 52 which may be coupled to a miniprocessor, counters, displays, etc. which accumulate and organize the data in accordance with the desired predetermined program for data routing and utilization.

Although considered conventional, one simplified form of ERR circuitry which may be used in FIG. 1 is shown in FIG. 2. On command from the pushbutton 38, the timing generator 36 first produces an erase enable function which turns a transistor 62 "ON" resulting in current flow $I_{ER}$ through the lower half of the magnetic head 44. Upon completion of the erase cycle, the timing generator 36 produces a record enable function which permits the flow of pulses 31 from the amplitude discriminator 28 to a transistor 64 via an AND gate 65. Current pulses $I_{RE}$ are produced in the upper half of magnetic head 44 which result in the magnetic medium switching from the erase remanence state to the opposite remanence state at the location of the pulses which are in turn coincident with the marks 17 of the grating 15. Upon completion of the record cycle both transistors 62 and 64 appear as open circuits and magnetic head 44 automatically reads the recorded flux pattern into a differential amplifier 66. The output of the differential amplifier 66 is processed through a shaping circuit 68 resulting in the generation of pulses which in turn are fed to a digital line driver 70 for transmission to the data routing logic 50 and 54. ERR circuitry 34 and 40 may be the same as described above.

Returning now to the operation of FIG. 1, when the system is conditioned to record, or store the marks 17 on the magnetic memory disk 42, a grating is positioned at the inspection plane of the system, which first will consist of a grating having a single slit in a black sheet, or vice versa. This single mark provides the proper position with respect to shaft rotation so as to produce a pulse referred to as once-per-facet (1/facet) which will condition the logic 50 to a predetermined state in readiness for the receipt of multiple marks when made available from ERR 34. With switches 32 and 37 positioned as shown in the drawing, this mark, which may be considered a synchronizing pulse, is recorded by means of magnetic head 46 on one track of the magnetic memory 42. Then another grating is placed in the inspection plane which includes a plurality of marks 17 which are utilized to delineate and divide the material being inspected into strips, segments, or lanes. As pointed out, this grating, as well as the previous one, may be as simple as providing pencil marks on the surface of the material 20 which, in effect, show up as flaws on the surface of the material, which appear on the display 35. In order to use the material itself, however, no other flaws can exist on the material in order to provide the proper positioning of the marks which are to be recorded. This will be readily apparent from the display 35. Of course, a separate grating 15 may be utilized with the material 20 removed so that the receiver 22 views only the grating 15.

It should also be pointed out that individual marks may be used to form the grating by placing a mark using a wire or any other suitable marker in the inspection plane, viewing the mark on the display 35 and if in the desired position, recording the mark so placed. A plurality of such marks may be recorded by moving the single mark to any position or a plurality of positions in the inspection plane. Furthermore, a signal generator may be used to artificially generate and record the marks on the magnetic memory 42 if desired, either individually or in a group.

With the grating 15 of the type desired positioned in the inspection plane, the receiver 22 is positioned to sense the transmission and the detection of the marks 17 (signals 25) which are applied from detector 24 through the analog processing circuitry 26 to the amplitude discriminator 28, producing an output thereof as shown by the signals 31. With switch 32 in the position shown and switch 37 in its alternate position, these signals are applied to the ERR circuitry 34 which are applied to the magnetic head 44 for recording on a second track of the magnetic memory disk 42. The recording is achieved merely by depressing pushbutton 38 which couples the timing generator 36 to the ERR circuitry 34 where timing generator 36 programs a sequence of commands to ERR circuitry 34 so that in one or more revolutions the track is erased followed by one or more revolutions of recording pulse train 31 on the track via the magnetic head 44. Since one revolution of the scanner 14 encompasses all facets, the recorded track includes the marks 17 for all facets of the rotary scanner 14 in precise registration to the facet responsible for scanning the grating 15, thus nulling any error which might be attributable to scanner 14 accuracy. Having so recorded the marks 17 on the magnetic disk 42, the magnetic head 44 reads back the recording as a succession of pulses which are shaped by the replay circuitry portion of the ERR circuitry 34 and presents these pulses to the data routing processing logic 50. Having concluded the program sequence, switch 32 is returned to its normal operative position, the grating 15 is removed, and the web of material of the type being inspected is placed in the inspection plane ready for inspection. The processing channel comprising the analog processor 26, amplitude discriminator 28, and any other flaw discriminators such as 30 are now again available for use in the inspection process. The feeding of the synchronizing pulse from circuitry 40 to the data routing logic along with the train of marks from the circuitry 34 is utilized to generate a series of gating functions on n different lines 52 at the output of the data routing logic 50.

A representative form of the data routing logic is shown in FIG. 3. The related timing diagram is shown in FIG. 4. The pulse called 1/f from circuitry 40 resets a counter 72 (e.g. Signetics 8281) to logic 0 on all outputs (A, B, C, D). This reset occurs in the blank or off-web zone of the scan. The reset insures that data formatting in lanes is always correct. The 8281 as a representative counter has 16 states, of which 8 are used in this example in order to provide 7 lanes of data routing. Only outputs A, B, and C are therefore used. Subsequent to the reset, pulses from the ERR 34, representing the routing positions, are applied to the clock 1 terminal of the counter 72. These pulses are thereby sequenced through their eight possible combinations by the counter 72 whose outputs are connected to the A, B, C inputs of an octal decoder 74 (e.g. Signetics 8250). The flaws in digital form, which are the output of the amplitude discriminator 28, are fed to the D input of decoder 74. The three inputs A, B, and C are decoded by the decoder 74 into one of 8 possible outputs (0 through 7). The 0 output is not used, since it corresponds to the reset condition. As each input state progresses from $A = 1$, $B = 0$, $C = 0$ through $A = 1$, $B = 1$, $C = 1$ in sequence and as a result of ERR pulses 1 through 7, the output lines 1 through 7 are sequentially enabled for periods corresponding to the time intervals between pulses 1 and 2, 2 and 3, . . . 7 and 8. A flaw input D of the decoder 74 will appear on the output line corresponding to the lane in which the flaw occurred, e.g. lanes 2 and 6 in FIG. 4. For the logic configuration shown, the output pulses fall from +5 v. to 0 v., sometimes referred to as negative logic.

Other forms of logic could be employed to obtain the same end result. The use of other available counters and decoders can also permit expanding the representative system to essentially any desired number of routed lanes.

FIG. 5 illustrates an alternate embodiment in which the record medium 60 is placed directly on a nonscanning surface of the rotary scanner 14. The system operation is the same.

What has thus been provided is a new method and apparatus for providing a magnetic encoder which is an integral part of the rotating optics of the system. The encoder is utilized for the placement of digital marks where required, which delineate lines along the length of the material being examined so that data with respect to those demarcated lines may be sorted and routed. By utilizing a suitable grating, the marks may be spatially placed where desired, and recorded with the marks being precisely correlated with the optical scan. At any time that the marks are desired to be changed, for example, when it is desired to change the division of the material being examined, or a different type or width of material is being inspected, a new grating can be installed at the inspection plane, the old marks erased, and new information recorded by a simple operation of a pushbutton switch. The relative simplicity of this method actually makes this technique the choice even where the material is only desired to be divided into two or three lanes or segments. The marks so generated are used to produce a commutating function, using known digital techniques such that one input signal source is distributed to a number of output ports.

Since other modifications and changes, varied to fit particular operating requirements and environments, will be apparent to those skilled in the art, this invention is not considered limited to the examples chosen for purposes of disclosure, and covers all changes and modifications which do not constitute departures from the true spirit and scope of this invention.

I claim:

1. A rotary scanner flaw detection system for detecting flaws in material being examined, comprising in combination
   a. a source of radiation
   b. a rotary scanner means for scanning said source in a predetermined scan path over the material being examined,
   c. a receiver having detector means positioned for receiving radiation applied by said source from the material being examined, said detector means producing signals in response to the intensity of the source of radiation applied thereto from the material,
   d. flaw discrimination means coupled to said detector means for passing flaw signals of predetermined characteristics in accordance with the requirements of said discriminator means,
   e. a record-bearing medium driven synchronously with said rotary scanner means,
   f. means for recording predetermined signals on said record-bearing medium which represent predetermined positions of said source in said predetermined scan path over the material being examined,
   g. data-routing logic circuit means coupled to said flaw discrimination means for sorting flaw signals applied thereto into predetermined outputs representing the occurrences of flaws on different predetermined sections of the material being examined,
   h. means for deriving said predetermined signals from said recording medium, and
   i. means for applying said predetermined signals to said data-routing logic circuit means, whereby said flaw signals are sorted and routed by said data sorting logic circuit means in accordance with the position of flaws in the material being examined.

2. The structure set forth in claim 1 wherein said record-bearing medium is a magnetic surface.

3. The structure set forth in claim 1 having a motor and a motor shaft, said rotating scanner means and said record-bearing medium being mounted on said motor shaft which are driven by said motor.

4. The structure set forth in claim 3 wherein said record-bearing medium is a magnetic disk or drum.

5. The structure set forth in claim 3 wherein said record-bearing medium is a magnetic surface positioned on a non-scanning surface of said rotary scanner means.

6. The structure set forth in claim 1 wherein said record-bearing medium is magnetic and said means for recording and deriving said predetermined signals comprises at least one magnetic head having erase, record, replay circuitry coupled thereto.

7. The method of providing flaw data information in accordance with the position of flaws occurring in the material being examined by a flaw detection system in which a source of radiation is scanned on a surface of material for locating flaws occurring thereon, comprising the steps of
   a. preparing a grating having grating marks thereon in predetermined positions which are capable of being detected by the flaw detection system,
   b. scanning said grating with a source of radiation in a predetermined scan pattern,
   c. detecting said grating marks in accordance with their predetermined position on said grating,
   d. synchronously recording marks representing the predetermined position of said grating marks in accordance with the scanning position of said source on said grating,
   e. scanning the surface of the material being examined for flaws and detecting flaws thereon,
   f. reading the recorded marks simultaneously with the scanning of the surface of material being examined, and
   g. sorting the flaws occurring in the material being examined in accordance with their position in the material by utilizing the recorded marks to delineate such positions.

8. The method set forth in claim 7 wherein the sorting of flaws is desired to be changed, comprising the steps of
   a. erasing the previously recorded marks,
   b. preparing a different grating having a different arrangement of grating marks thereon,
   c. scanning said different grating and recording said different arrangement of grating marks,
   d. scanning the material for flaws and simultaneously reading the different arrangement of recorded marks, and
   e. sorting the flaws using the different arrangement of recorded marks.

* * * * *